United States Patent
Heimburger et al.

(12) 
(10) Patent No.: US 6,346,277 B1
(45) Date of Patent: Feb. 12, 2002

(54) PROCESS FOR THE PASTEURIZATION OF PLASMA OR CONCENTRATES OF BLOOD COAGULATION FACTORS II, VII, IX AND X

(75) Inventors: Norbert Heimburger, Marburg; Gerhardt Kumpe, Wetter; Wilfried Wormsbächer, Kirchhain; Hans Martin Preis, Marburg, all of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 08/415,166

(22) Filed: Mar. 31, 1995

Related U.S. Application Data

(63) Continuation of application No. 08/239,851, filed on May 9, 1994, now abandoned, which is a continuation of application No. 07/898,362, filed on Jun. 12, 1992, now abandoned, which is a continuation of application No. 07/732,432, filed on Jul. 18, 1991, now abandoned, which is a continuation of application No. 07/127,561, filed on Dec. 2, 1987, now abandoned, which is a continuation of application No. 06/658,028, filed on Oct. 5, 1984, now abandoned.

(30) Foreign Application Priority Data

Oct. 8, 1993 (DE) .......................................... 33 36 631

(51) Int. Cl.⁷ ............................................... A61K 35/16
(52) U.S. Cl. ........................ 424/530; 435/236; 435/238; 435/2; 514/802; 530/304
(58) Field of Search ................................. 435/236, 238, 435/2; 514/802; 424/530; 530/384

(56) References Cited

U.S. PATENT DOCUMENTS

| | | | |
|---|---|---|---|
| 4,314,997 A | | 2/1982 | Shanbrom |
| 4,315,919 A | | 2/1982 | Shanbrom |
| 4,364,861 A | * | 12/1982 | Mitra et al. .............. 260/112 B |
| 4,391,746 A | * | 7/1983 | Mitra et al. .............. 260/112 B |
| 4,404,187 A | * | 9/1983 | Schwinn et al. ............. 424/101 |
| 4,405,603 A | * | 9/1983 | Schwinn et al. ............. 424/101 |
| 4,412,985 A | | 11/1983 | Shanbrom |
| 4,562,072 A | | 12/1985 | Heimburger et al. |
| 5,371,195 A | * | 12/1994 | Grandgeorge et al. ....... 530/383 |
| 5,378,365 A | * | 1/1995 | Arriaghi et al. ............. 210/635 |

OTHER PUBLICATIONS

Steinbuch et al., "Chem Abstracts," vol. 66:9221p, 1967.*
The Merck Index, 10th ed., p. 508, 1983.*
"Hemostatic fraction of the plasma containing four factors (II, VII, IX, X) of the blood coagulation system." M. Steinbuch and J.P. Soulier (Natl. Center Blood Transfusion, Paris). *Probl. Gematol. Pereliv. Krovi* (11(20), 15–21 (1966) (Russ.).
Steinbuch et al, Cited in Chem. Abstracts vol. 66:9221 p. 1967.*
The Merck Index, 10th Ed. "Edetate Calcium Disodium" p. 508 1983.*

* cited by examiner

*Primary Examiner*—Chhaya D. Sayala
(74) *Attorney, Agent, or Firm*—Finnegan, Henderson, Farabow, Garrett & Dunner, L.L.P.

(57) ABSTRACT

The present invention relates to a process for the preparation of a product of blood coagulation factors II, VII, IX and X which is virtually free of virus, the process comprising heating an aqueous liquid containing these factors in the presence of calcium ions and a chelating agent and, optionally, an amino acid, a saccharide or sugar alcohol, antithrombin III and/or heparin. The product can be used for the treatment of blood coagulation disorders.

17 Claims, No Drawings

PROCESS FOR THE PASTEURIZATION OF PLASMA OR CONCENTRATES OF BLOOD COAGULATION FACTORS II, VII, IX AND X

This application is a continuation, of application Ser. No. 08/239,851, filed May 9, 1994, now abandoned, which is a continuation of Ser. No. 07/898,362, filed Jun. 12, 1992, abandoned, which is a continuation of application Ser. No. 07/732,432, filed Jul. 18, 1991, abandoned, which is a continuation of Ser. No. 07/127,561, filed Dec. 2, 1987, abandoned, which is a continuation of application Ser. No. 06/658,028 filed Oct. 5, 1984, abandoned.

BACKGROUND OF THE INVENTION

1. Field of the Invention

The invention relates to a process for the preparation of a plasma product which is virtually free from active viruses or of a concentrate of blood coagulation factors II, VII, IX and X which is virtually free from such viruses, by heating in the presence of stabilizers, and to a product of these factors which is thereby prepared. Such products can be used for the treatment of blood coagulation disorders.

2. Description of the Prior Art

Coagulation of blood is a complex process which proceeds in stages and is triggered of by various physiological and pathological causes, its course depending on about 20 promoting or inhibiting factors. Disorders in blood coagulation, some of which manifest themselves as diseases, occur as a result of a reduction or increase in these blood coagulation factors.

Concentrates of factors II, VII, IX and X are suitable for the treatment of various congenital or acquired disorders in the synthesis of these factors. The treatment of patients with concentrates of these factors has hitherto been associated with the risk of transmission of viruses and, in particular, hepatitis.

Albumin is hepatitis-safe if it is heated to 60° C. in aqueous solution and in the presence of stabilizers (Gellis, S. S. et al., J. Clin. Invest. (1948) 27, 239). It is therefore to be assumed that a concentrate of factors II, VII, IX and X heated in the presence of suitable stabilizers is likewise hepatitis-safe.

German Offenlegungsschrift 2,916,711 describes a process for the heat-stabilization of other coagulation factors in aqueous solution by addition of an amino acid and a mono- or oligo-saccharide or sugar-alcohol.

However, inactivation of factors II, VII, IX and X during heating cannot be prevented in this way. The observation that factors II and VII can be protected from thermal inactivation in aqueous solution by chelating agents (German Patent 3,043,857 A1) and factors IX and X can be protected by calcium (German Patent 3,045,153 A1). was therefore an advance. However, neither process allows the preparation of a product of all four factors in one operating process, as is desirable, since all four factors are reduced in cases of vitamin K deficiency or under therapy with oral anti-coagulants and must therefore be replaced at the same time.

SUMMARY OF THE INVENTION

Accordingly, there was the object of discovering a process for stabilizing an aqueous solution containing factors II, VII, IX and X from thermal inactivation.

Surprisingly, it has now been found that an aqueous solution containing all four factors II, VII, IX and X can be protected From the adverse consequences of heat treatment by addition of calcium ions and a chelating agent. If appropriate, antithrombin III (AT) and heparin can be added in order to prevent activation of factors II and VII. The preconditions were thus provided for preparing these four factors, with a high purity, and yield arid containing no active viruses, in one operation.

The chelating agent is added in addition to the citrate already present.

It is surprising that a mixture of calcium ions and chelating agent effects the desired protection of all factors II, VII, IX and X from toss in activity by heating, although, according to German Patent 3,043,857, a chelating agent is advantageous for protecting factors II and VII, whitst calcium ions are used for the same purpose for factors IX and X (German Patent 3,045,153), and chelating agents also form complexes with calcium ions. In each case only the two corresponding factors should therefore be protected from degradation by heat, and not all four, depending on whether the chelating agent or the calcium ions are present in excess.

DESCRIPTION OF PREFERRED EMBODIMENTS

The invention thus relates to a process for the preparation of a virtually virus-free and hepatitis-safe product of blood coagulation factors II, VII, IX and X by heating an aqueous solutions if appropriate in the presence of an amino acid and/or a saccharide or sugar-alcohol, which comprises heating the solution in the presence of calcium ions and a chelating agent and, if appropriate, antithrombin III and/or heparin.

Such a solution can be a solution containing these factors or a concentrate containing these, as well as plasma or a plasma or placenta fraction.

The optimum concentration of calcium ions is in the range from 1 to 50 mmol/l, preferably 25 to 50 mmol/l.

Examples of suitable salts which supply calcium ions are the chloride, acetate or nitrate, and all water-soluble calcium salts of sugar-acids, such as gluconic acid or lactonic acid. The chloride and acetate are preferably used.

Examples of suitable chelating agents are: ethylenediamino-tetraacetic acid (EDTA), ethylene glycol bis-(2-aminoethyl ether)-tetraacetic acid (EGTA), diaminocyclohexane-tetraacetic acid (CDTA), diaminopropane-tetraacetic acid and nitrilotriacetic acid, and, in particular, soluble alkali metal salts thereof.

Aliphatic aza-tri- or -tetra-carboxylic acids with 6–20 carbon atoms and 1 or 2 nitrogen atoms and soluble alkali metal salts thereof and, in particular, the sodium salts of ethylenediaminotetraacetic acid (EDTA) or ethylene glycol bis-(2-amino-ethyl ether)-tetraacetic acid (EGTA) are preferably used. The optimum concentration of the chelating agents is 1 to 20 mmol/l, preferably 5 mmol/l.

Mixtures of 25 mmol/l of calcium with 5 mmol/l of EDTA have proved particularly suitable.

Antithrombin III is employed in a concentration of 0.05–2 units/ml, based on the activity of 1 ml of citrated mixed plasma (1 unit), and together with heparin in concentrations of 0.5–2 ) USP units/ml, preferably 0.2 unit of antithrombin III with 2 USP units of heparin.

In the presence of a mixture of calcium ions and a chelating agent and, if appropriate, the antithrombin III-heparin complex, the aqueous solution of the coagulation factors can be heated until, according to the current state of knowledge, transmission of viruses, and in particular hepatitis pathogens, can be virtually excluded. This particularly applies if the pasteurization is combined with adsorption and precipitation processes, in which the active compound remains in the supernatant liquor and the hepatitis viruses can be separated off together with the insoluble precipitate. A product which has been kept at about 60° C. in aqueous solution for at least 10 hours is at present regarded as virtually hepatitis-safe, especially if the starting material is human tissue fluid in which hepatitis viruses have not been detected by a third generation test.

A particularly preferred embodiment of the invention comprises adding to a solution containing all four factors, preferably plasma or a plasma or placenta fraction, 0.2–2 units/ml of antithrombin III, 2–20 USP units/ml of heparin, 25–50 mmol/l of calcium ions and 1–20 mmol/l of EDTA, 1–3 mol/l of at least one of the amino acids glycine, alpha- or beta-alanine, lysine, leucine, valine, asparagine, serine, hydroxyprotine, protine, glutamine or alpha-, beta- or gamma-aminobutyric acid, but preferably glycine, and 20 to 60 g/100 g of solution of a mono- or oligo-saccharide or sugar-alcohol, preferably 1 to 3 mol/l of glycine and 20 to 60 g/100 g of solution of sucrose, heating the mixture to a temperature of 30° C. to 100° C., preferably 60° C. to 100° C. and keeping it at this temperature for 1 minute to 48 hours, preferably 8–12 hours, the shortest time being matched with the highest temperature and vice versa.

A pH value of 6 to 8 is maintained. A virtually virus-free product of factors II, VII, IX and X is obtained in this manner.

Depending on the solubility of the calcium salt, the amino acid or the carbohydrate, the corresponding concentrations of 0.3 and 3.0 mol/l and 60 g/100 g can be extended to higher concentrations if the calcium salt, the aminoacid or the carbohydrate have a correspondingly higher solubility at the desired temperature. The temperature treatment can also be carried out in several successive steps.

A hepatitis-safe product is achieved with the preferably used combination of antithrombin III, heparin, calcium chloride and EDTA with glycine and sucrose by heating.

In order to obtain a virus-free plasma which contains factors II, VII, IX and X in natural and active form, a mixture of a chelating agent, preferably EDTA, and calcium ions, preferably in amounts such that these are present in concentrations of 5 mmol/l of EDTA and 25 mmol/l of calcium chloride, is added to the plasma and the mixture is heated to 60° C. in a sucrose (60 g/100 g)/glycine (2 mol/l) mixture and kept at this temperature for 10 hours.

In order to obtain a natural and active concentrate of factors II, VII, IX and X, a mixture of a chelating agent, preferably EDTA and calcium ions, preferably in concentrations of 5 mmol/l of EDTA and 25 mmol/l of calcium chloride, is added to the plasma or placenta fraction, advantageously a fraction in which the factors to be stabilized are concentrated. After addition of antithrombin III, preferably 0.2 unit/ml, and heparin, preferably 2 USP units/ml, the mixture is kept in sucrose (60 g/100 g)/glycine (2 mol/l) and heated 10 h to 60° C.

Such a fraction is obtained, for example, by the method of Soulier et al., Thrombosis Diath. Haemorrh. Suppl. 35, 61 (1969). For this, plasma which has been obtained from blood anti-coagulated with 0.01 mol/l of EDTA is adsorbed onto calcium phosphate and the solid is centrifuged off. The factors are thereby bonded quantitatively to the adsorbent and can be isolated by eluting several times with 0.2 mol/l of tri-sodium citrate. The combined eluates are further purified by combined alcohol and acetic acid precipitation at temperatures of −8° C. to +4° C. The factors are thereby at the same time concentrated.

The concentrate is taken up in a suitable buffer, advantageously sodium chloride/sodium citrate containing 0.06 and, respectively, 0.02 mol/l and with a pH of 7.5.

The coagulation factors can be recovered from the heated solution and purified by precipitation with ammonium sulfate at 30–45% saturation, adsorption of the supernatant liquor onto 0.4 to 1 g/100 ml of calcium phosphate and elution.

The monitoring of the measures for the enrichment and purification of factors II, VII, IX and X is familiar to the expert from the knowledge of determination methods for the substances in question. Using these monitoring methods, the process conditions can be controlled in respect of a satisfactory yield and satisfactory purity of the product.

Factor II can be determined, for example, by the method of Koller, F. et al., Dtsch. med. Wschr. 81, 516 (1956). For this, one part, for example 0.1 ml, of factor II-deficient plasma and one part of dilute normal plasma are mixed. This mixture is kept at +37° C. for 30 seconds. Thereafter, two parts of calcium-containing thromboplastin, for example prepared according to German Patent 2,356,493, are added and the time which elapses before a coagulum appears is determined. For a quantitative determination, the coagulation time resulting from the solution containing factor II is read off with reference to a calibration curve obtained with a normal plasma dilution series.

One unit of factor II corresponds to the factor II activity of 1 ml of normal plasma.

Factor VII can be determined, for example, by the method of Koller, F. et al., Acta haemat. 6, 1 (1951). For this, one part, for example 0.1 ml, of factor VII-deficient plasma and one part of dilute normal plasma are mixed. This mixture is kept at +37° C. for 30 seconds. Thereafter, two parts of calcium-containing thromboplastin, for example prepared according to German Patent 2,356,493, are added and the time which elapses before a coagulum appears is determined. For quantitative determination, the coagulation time result in from the solution containing factor VII is read off with reference to a calibration curve obtained with a normal plasma dilution series.

One unit of factor VII corresponds to the factor VII activity of 1 ml of normal plasma.

Factor IX is determined, for example, by the following method:

1 part, for example 0.1 ml, of partial thromboplastin, for example prepared according to German Auslegeschrift 2,316,430, is mixed with one part of factor IX-deficient plasma and one part of dilute normal plasma. This mixture is kept at 37° C. for 6 minutes. After addition of one part of a 0.025 molar calcium chloride solution which has been prewarmed to 37° C., the time which elapses between the addition of the calcium chloride solution and the appearance of a coagulum is determined. For quantitative determination, the coagulation time resulting from the solution containing factor IX is read off with reference to a calibration curve obtained with a normal plasma dilution series.

1 international unit (=1 IU) of factor IX corresponds to the factor IX activity of 1 ml of normal plasma.

Factor X can be determined, for example, by the method of Duckert et al., Blood Coagulation, Hemorrhage and Thrombosis, Ed. Tocantins, L. M. and Kazal, L. A. (1964). For this, one part, for example 0.1 ml, of factor X-deficient plasma and 1 part of dilute normal plasma are mixed. This mixture is kept at +37° C. for 30 seconds. Thereafter, two parts of calcium-containing thromboplastin, for example prepared according to German Patent 2,356,493, are added and the time which elapses before a coagulum appears is determined. For quantitative determination, the coagulation time resulting from the solution containing factor X is read off with reference to a calibration curve obtained with a normal plasma dilution series. One unit of factor X corresponds to the factor X activity of 1 ml of normal plasma.

To destroy the hepatitis viruses, calcium ions, EDTA, glycine and sucrose and, if appropriate, antithrombin III and heparin are added to the solution and the mixture is heated.

After pasteurization (10 hours, 60° C.) of human plasma, following addition of sucrose (60 g/100 g) and glycine (2 mol/l) and in the presence of 25 mmol/l of calcium chloride and 5 mmol/l of EDTA, the following activities, based on the plasma employed, were found: F II 90%, F VII 85%, F IX 83%, F X 80%.

The influence the various stabilizers have on obtaining the activity of the individual prothrombin factors in a plasma of placenta fraction on heating can be seen from Table I. Pasteurization with sucrose and glycine alone gives a poor F IX yield. However, this is highly disadvantageous, since the prothrombin concentrate is chiefly used for therapy of hemophilia B. The additional use of calcium ions without a chelating agent in a concentration of 6.25 mmol/l leads to an activation of F VII and F IX and also reduces the yields of F II and F X. Such a product would be unsuitable for use on humans because of a possible risk of thrombosis. If EDTA is used without calcium ions in a concentration of 5 mmol/l, in addition to sucrose and glycine, poor F IX and F X yields are achieved, with good F II and F VII yields. The prothrombin factors cannot be stabilized merely with antithrombin III, heparin, sucrose and glycine.

The best result is given by the combination of calcium ions with EDTA with addition of antithrombin III and heparin with sucrose and glycine. Under these conditions, the yields for all four factors are of the order of about 80% and the product is also free from activated factors and thrombin.

The concentrations of coagulation factors in an aqueous solution with which the process described can be carried out are, in particular, in the following ranges: factor II: 0.3 to 50 units/ml; factor VII: 0.3 to 30 units/m; factor IX: 0.5 to 60 units/ml; and factor X: 0.4 to 60 units/m.

Particularly preferred ranges are 0.5 to 25 for factor II, 0.5 to 15 for factor VII, 0.7 to 30 for factor IX and 0.6 to 30 for factor X.

A solution which contains the active compounds—i.e. in the present case the coagulation factors—in concentrations which are higher than those of the natural starting materials is usually designated a concentrate.

TABLE I

| Additives | | | | | | Coagulation activity after heating (10 hours, 60° C.) in %, based on the starting material | | | |
|---|---|---|---|---|---|---|---|---|---|
| Sucrose | Glycine | Ca ions | EDTA | AT III | Heparin | F II | F VII | F IX | F X |
| g/100 g | mol/l | mmol/l | mmol/l | units/ml | USP units/ml | | | | |
| 60 | 2 | — | — | — | — | 83 | 58 | 25 | 43 |
| 60 | 2 | 6.25 | — | — | — | 47 | act.* | act.* | 40 |
| 60 | 2 | — | 5 | — | — | 73 | 61 | 41 | 50 |
| 60 | 2 | 25 | 5 | 0.2 | 2 | 72 | 83 | 83 | 87 |
| 60 | 2 | — | — | 0.2 | 2 | 72 | 55 | 48 | 33 |

*act. = activated

For further purification, the heated solution can be centrifuged, if appropriate. Impurities can be removed by precipitation with ammonium sulfate and 30–45% saturation.

It is then possible to adsorb the supernatant liquor onto 0.04 to 1.0 g of calcium phosphate per 100 ml of solution, to wash the loaded adsorbent and elute it with citrate buffer and to dialyze the eluate.

For use on humans, the product can be subjected to sterilization by filtration.

The invention particularly relates to a product of factors II, VII, IX and X which is free from active viruses and can be obtained by this process.

It is advantageous to add protein-stabilizing substances, for example proteins, aminoacids or carbohydrates, to the product in order to increase the storage stability. Finally, the product subjected to this treatment can be supplied in freeze-dried form, in which case the addition of anticoagulants, such as, for example, heparin, may be advantageous.

The product according to the invention, in particular the product in the form of a concentrate, is, in a solution suitable for pharmaceutical administration, a medicament for the treatment of coagulopathy and can be used intravenously, advantageously as an infusion, for the therapy and prophylaxis of hemorrhages caused by factor deficiency.

In the form of a lyophilized, coagulation-promoting plasma, the pasteurized product covers the indications of fresh-frozen plasma, for example topping up of the blood volume, maintenance of the oncotic pressure, blood loss after major operations and accidents and treatment of various forms of shock and first aid for polytraumatized patients.

The invention may be illustrated by the examples which follow.

EXAMPLE 1

1,000 ml of human citrated plasma were warmed to 25–30° C., with stirring, and 20 ml of a solution which contained 1.86 g of EDTA and had been brought to pH 7.8 with 2 N NaOH, were added. 10 minutes thereafter, 1,000 g of sucrose were stirred slowly into the solutions which had been warmed to 30° C. After the sucrose had been dissolved, 150 g of crystalline glycine were added slowly, with stirring; after the solid had dissolved completely, 25 ml of 1 molar CaCl$_2$ solution were added and the solution was brought to pH 7.2 with 2 N NaOH. The solution, which had been increased to 1.7 l by the stabilizers, was heated at 60° C. in a waterbath for 10 hours, and was also clear after the heating.

Removal of the Stabilizers:

After cooling of the pasteurized solution, this was clarified by filtration over a 3.0 and 1.2 μ Sartorius membrane filter; the solution was then diluted to 5 l with a citrate/NaCl buffer (0.01 mol/l of tri-Na citrate, pH 7.5; 0.06 mol/l of NaCl) and dialyzed on an ultrafiter, with simultaneous concentration, 3 times against 5 l of a buffer of the same composition and concentrated to 1,000 ml.

After the plasma starting volume of 1,000 ml had been reached, the clear solution was clarified and sterilized by filtration over a Sartorius membrane filter, bottled in 50 ml volumes and lyophilized. The following activities, based on standard human plasma, were found in the dried material reconstituted with 50 ml of distilled water: F II 87%, F VII 81%, F IX 83%, F X 80%.

EXAMPLE 2

1. Isolation of the Prothrombin Factors by Adsorption onto DEAE-Sephadex® and Elution DEAE-Sephadex® A 50 (0.6 g/l), which contained 5 mmol/l of EDTA in physiological sodium chloride solution and had been equilibrated at pH 6, were added to 550 l of citrated plasma. The suspension was stirred at 15° C. for 60 minutes, for adsorption. After sedimentation of the adsorbent, the supernatant liquor was siphoned off and the DEAE-Sephadex® with the adsorbed factors was washed with 50 l of physiological sodium chloride solution containing 5 mmol/l of EDTA until it was free from contaminating proteins. The adsorbent was then stirred with 7 l of 1 mol/l of NaCl, pH 8, containing 5 mmol/l of EDTA and was separated off by centrifugation and discarded.

2. Pasteurization 0.2 units of AT III/ml and 2 units/ml of heparin were added to the supernatant liquor. 1,050 g of solid glycine were then added and, after-this had dissolved, 25.7 g of $CaCl_2 \cdot 2H_2O$, corresponding to a final concentration of 25 mmol/l, were introduced. After a constant pH value of 7.2 had been reached, the solution was heated to 30 to 37° C. and 10.5 kg of sucrose (final concentration about 60 g/100 g of solution) were added. After the pH value of this highly viscous solution had once again been brought to 7.2, the solution was heated at 60° C. in a waterbath for 10 hours.

3. Removal of Undesired Proteins by Precipitation with Ammonium Sulfate

The pasteurized solution, about 14 l, was cooled to room temperature and added to 31.5 l of distilled water containing 334 g of $CaCl_2 \cdot 2H_2O$, corresponding to a final concentration of 50 mmol/l.

24.5 l of saturated ammonium sulfate solution were introduced into this solution of the prothrombin factors at pH 7.5 and the precipitate was centrifuged off and discarded.

4. High Purification of the Prothrombin Factors by Adsorption onto Calcium Phosphate 700 g of solid $Ca_3(PO_4)_2$ were added, at pH 7.6, to the supernatant liquor containing the prothrombin factors and the mixture was stirred at room temperature for 20 to 30 minutes. The calcium phosphate was isolated by centrifugation and washed three times with 20 l of a solution of 0.5 mol/l of NaCl and 1 g/100 ml of glycine, pH 7.6.

The prothrombin factors were eluted from the adsorbent with 750 ml of a buffer containing 0.2 mol/l of trisodium citrate, 0.15 mmol/l of NaCl, 1 g/100 ml of glycine, 0.6 units/ml of AT III and 28 units/ml of heparin (pH about 7.5), by stirring (20 minutes) at room temperature. The eluate was freed from coarse particles by centrifugation at 3,000 g.

5. Formulation 0.15 g/100 ml of AEROSIL® was added to the supernatant liquor and the mixture was freed from solids by ultracentrifugation at 30,000 g. Aerosil® is a highly disperse silicic acid produced by the hydrolysis of $SiCl_4$ in an oxyhydrogen flame ($2H_2+O_2+SiCl_4 \rightarrow SiO_2+HCl$). About 0.6 g of human albumin per 100 ml of liquid were added to the clear supernatant liquor and the mixture was brought to pH 6.8 and dialyzed against 50 l of physiological sodium chloride solution for 3 hours. The solution was brought to about 60 units of F IX, 60 units of F II, 50 units of F X and 25 units of F VII, sterilized by filtration, bottled in 5 ml volumes and lyophilized.

What is claimed is:

1. A process for the preparation of a virus-free product of blood coagulation factors II, VII, IX and X comprising heating an aqueous solution containing these factors to a temperature ranging from 30° C. to 100° C. for a period ranging from 1 minute to 48 hours, in the presence of at least one compound selected from the group consisting of an amino acid, a saccharide and a sugar-alcohol and also in the presence of calcium ions and a chelating agent, wherein the concentration of calcium ions is from 1 to about 30 mmol/l and the concentration of the chelating agent is from 1 to about 7 mmol/l.

2. The process of claim 1 wherein the concentration of calcium ions is 25 mmol/l and the concentration of chelating agent is 5 mmol/l.

3. The process as claimed in claim 1, wherein the chelating agent is an aliphatic aza-tri- or -tetra-carboxylic acid with 6 to 20 carbon atoms and 1 or 2 nitrogen atoms, or a soluble alkali metal salt thereof.

4. The process as claimed in claim 1, wherein the aqueous solution is citrated plasma, a plasma fraction or a placenta fraction.

5. The process as claimed in claim 1, wherein the aqueous solution is a concentrate of factors II, VII, IX and X.

6. The process is claimed in claim 1, wherein said solution includes at least one compound selected from the group consisting of antithrombin III and heparin.

7. The process as claimed in claim 6, wherein the solution is heated in the presence of 0.2–2 units/ml of antithrombin III, 2–20 USP units/ml of heparin, 25 to 30 mmol/l of calcium ions, 1 to 7 mmol/l of EDTA, 1–3 mol/l of at least one amino acid selected from the group consisting of glycine, alpha-alanine, beta-alanine, lysine, leucine, valine, asparagine, serine, hydroxyproline, proline, and glutamine or one substance selected from the group consisting of alpha-aminobutyric acid, beta-aminobutyric acid and gamma-aminobutyric acid, and 20 to 60 g/100 g of a solution of a mono-saccharide, oligo-saccharide or sugar-alcohol.

8. The process of claim 7, wherein said amino acid is glycine.

9. The process of claim 7, wherein the solution is heated in the presence of 1 to 3 mol/l of glycine and 20 to 60 g/100 g of a solution of sucrose.

10. The process of claim 7, wherein said solution is heated to a temperature ranging from 60° C. to 100° C.

11. The process of claim 9, wherein said solution is heated to a temperature ranging from 60° C. to 100° C.

12. The process of claim 7, wherein said solution is heated for a period ranging from 8 hours to 12 hours.

13. The process of claim 9, wherein said solution is heated for a period ranging from 8 hours to 12 hours.

14. The process of claim 10, wherein said solution is heated for a period ranging from 8 hours to 12 hours.

15. The process of claim 11, wherein said solution is heated for a period ranging from 8 hours to 12 hours.

16. The process of claim 1 wherein the concentration of calcium ions is 25 mmol/l.

17. The process of claim 1 wherein the concentration of chelating agent is 5 mmol/l.

* * * * *